US00PP22939P2

(12) United States Plant Patent
Bernuetz

(10) Patent No.: US PP22,939 P2
(45) Date of Patent: Aug. 7, 2012

(54) ***SCAEVOLA* PLANT NAMED 'BONSCA7200'**

(50) Latin Name: *Scaevola aemula*
Varietal Denomination: Bonsca7200

(75) Inventor: Andrew Bernuetz, Silverdale (AU)

(73) Assignee: Bonza Botanicals Pty. Ltd., Yellow Rock, NSW (AU)

( * ) Notice: Subject to any disclaimer, the term of this patent is extended or adjusted under 35 U.S.C. 154(b) by 0 days.

(21) Appl. No.: 13/136,894

(22) Filed: Aug. 12, 2011

(51) Int. Cl.
*A01H 5/00* (2006.01)

(52) U.S. Cl. ..... Plt./363

(58) Field of Classification Search ..... Plt./363
See application file for complete search history.

*Primary Examiner* — June Hwu
*Assistant Examiner* — Louanne Krawczewicz Myers
(74) *Attorney, Agent, or Firm* — C. A. Whealy

(57) ABSTRACT

A new and distinct cultivar of *Scaevola* plant named 'Bonsca7200', characterized by its compact, mounded and trailing plant habit; vigorous growth habit; freely branching habit; early and freely flowering habit; long flowering period; violet-colored flowers; and good container and garden performance.

1 Drawing Sheet

Botanical designation: *Scaevola aemula*.
Cultivar denomination: 'BONSCA7200'.

BACKGROUND OF THE INVENTION

The present invention relates to a new and distinct cultivar of *Scaevola* plant, botanically known as *Scaevola aemula* and hereinafter referred to by the name 'Bonsca7200'.

The new *Scaevola* plant a product of a planned breeding program conducted by the Inventor in Yellow Rock, New South Wales, Australia. The objective of the breeding program is to create new vigorous and freely-flowering *Scaevola* plants with compact plant habit and attractive flower color.

The new *Scaevola* plant originated from an open-pollination in Yellow Rock, New South Wales, Australia in early 2004 of a proprietary selection of *Scaevola aemula* identified as code number 04-28, not patented, as the female, or seed, parent with an unknown proprietary selection of *Scaevola aemula*, as the male, or pollen, parent. The new *Scaevola* plant was discovered and selected by the Inventor as a single flowering plant from within the progeny of the stated open-pollination in a controlled environment in Yellow Rock, New South Wales, Australia in March, 2005.

Asexual reproduction of the new *Scaevola* plant by vegetative cuttings in a controlled environment in Yellow Rock, New South Wales, Australia since April, 2005 has shown that the unique features of this new *Scaevola* plant are stable and reproduced true to type in successive generations.

SUMMARY OF THE INVENTION

Plants of the new *Scaevola* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Bonsca7200'. These characteristics in combination distinguish 'Bonsca7200' as a new and distinct *Scaevola* plant:

1. Compact, mounded and trailing plant habit.
2. Vigorous growth habit.
3. Freely branching habit.
4. Early and freely flowering habit.
5. Long flowering period.
6. Violet-colored flowers.
7. Good container and garden performance.

Plants of the new *Scaevola* can be compared to plants of the female parent selection. Plants of the new *Scaevola* differ from plants of the female parent selection in the following characteristics:

1. Plants of the new *Scaevola* are more vigorous than plants of the female parent selection.
2. Plants of the new *Scaevola* and the female parent selection differ in flower color as plants of the female parent selection have dark blue-colored flowers.

Plants of the new *Scaevola* can be compared to plants of the *Scaevola aemula* 'Bonscalib', disclosed in U.S. Plant Pat. No. 19,516. In side-by-side comparisons, plants of the new *Scaevola* differed from plants of the 'Bonscalib' in the following characteristics:

1. Plants of the new *Scaevola* were more trailing than plants of 'Bonscalib'.
2. Plants of the new *Scaevola* were more vigorous than plants of 'Bonscalib'.
3. Plants of the new *Scaevola* had larger leaves than plants of 'Bonscalib'.
4. Flowers of plants of the new *Scaevola* had broader petals than flowers of plants of 'Bonscalib'.
5 Flowers of plants of the new *Scaevola* were darker violet in color than flowers of plants of 'Bonscalib'.

BRIEF DESCRIPTION OF THE PHOTOGRAPHS

The accompanying colored photographs illustrate the overall appearance of the new *Scaevola* plant showing the colors as true as it is reasonably possible to obtain in colored reproductions of this type. Colors in the photographs may differ slightly from the color values cited in the detailed botanical description which accurately describe the colors of the new *Scaevola* plant.

The photograph at the top of the sheet comprises a side perspective view of a typical flowering plant of 'Bonsca7200' grown in a container.

The photograph at the bottom of the sheet is a close-up view of typical flowers and leaves of 'Bonsca7200'.

DETAILED BOTANICAL DESCRIPTION

The aforementioned photographs and following observations, measurements and values describe plants grown in 15-cm containers during the summer in an outdoor nursery in Higashiomi, Shiga, Japan and under environmental conditions and cultural practices which closely approximate commercial production. During the production of the plants, day temperatures averaged 23° C. and night temperatures averaged 13° C. Plants were four months old when the photographs were taken and five months old when the detailed description was taken. In the following description, color references are made to The Royal Horticultural Society Colour Chart, 2001 Edition, except where general terms of ordinary dictionary significance are used.

Botanical classification: *Scaevola aemula* 'Bonsca7200'.

Parentage:

*Female, or seed, parent*.—Proprietary selection of *Scaevola aemula* identified as code number 04-28, not patented.

*Male or pollen parent*.—Unknown proprietary selection of *Scaevola aemula*, not patented.

Propagation:

*Type*.—By vegetative cuttings.

*Time to initiate roots, summer*.—About seven days at 20° C. to 25° C.

*Time to initiate roots, winter*.—About ten days at 15° C. to 20° C.

*Time to develop roots, summer*.—About three weeks at 20° C. to 25° C.

*Time to develop roots, winter*.—About four weeks at 15° C. to 20° C.

*Root description*.—Fine, fibrous; white in color.

*Rooting habit*.—Freely branching; moderately dense.

Plant description:

*Plant form and growth habit*.—Compact, mounded and trailing plant habit; vigorous growth habit.

*Branching habit*.—Freely branching, lateral branches potentially forming at every node; pinching enhances branching potential.

*Plant height*.—About 10.3 cm.

*Plant diameter* (*area of spread*).—About 48.5 cm.

Lateral branch description:

*Length*.—About 23.3 cm.

*Diameter*.—About 2.8 mm.

*Internode length*.—About 1.4 cm.

*Aspect*.—Outwardly, decumbent.

*Texture*.—Pubescent.

*Color*.—Close to 144B overlain with close to 200B.

Foliage description:

*Arrangement*.—Alternate, simple.

*Length*.—About 7.3 cm.

*Width*.—About 2.7 cm.

*Shape*.—Narrowly spatulate.

*Apex*.—Obtuse to mucronate.

*Base*.—Cuneate.

*Margin*.—Serrate.

*Texture, upper and lower surfaces*.—Pubescent; slightly coarse.

*Venation pattern*.—Pinnate, reticulate.

*Color*.—Developing and fully expanded leaves, upper surface: Close to 137B, towards the margins, tinted with close to 166A; venation, close to 144C. Developing and fully expanded leaves, lower surface: Close to 138B; venation, close to 144C tinted with close to 166A.

*Petiole length*.—About 2.2 cm.

*Petiole diameter*.—About 4 mm.

*Petiole texture, upper and lower surfaces*.—Pubescent.

*Petiole color, upper and lower surfaces*.—Close to 144B tinted with close to 166A.

Flower description:

*Flower type and shape*.—Zygomorphic, semi-circular, fan-shaped flowers with five petals fused at the base to form a tubular flower throat; flower throat open along the upper surface exposing reproductive organs.

*Flower arrangement and quantity*.—Solitary sessile flowers arising from leaf axils; flowers face upright to outwardly; freely flowering habit with typically about 14 flowers developing per lateral branch.

*Flowering time*.—Plants begin flowering after about four weeks after planting; long flower period, plants flower continuously from spring to late autumn in Japan.

*Flower longevity*.—Flowers typically last about a week on the plant; flowers persistent.

*Fragrance*.—None detected.

*Flower buds*.—Shape: Elongated ovate. Length: About 1 cm. Diameter: About 2.6 mm. Color: Close to N78B.

*Flowers*.—Diameter: About 2.5 cm by 3.2 cm. Tube length: About 8.4 mm. Tube diameter: About 3.5 mm.

*Petals*.—Quantity: Five, fused at base. Shape: Narrowly elliptic. Apex: Cuspidate. Margin: Entire. Length, above tube: About 1.4 cm. Width, above tube: About 6.5 mm. Texture, upper and lower surfaces: Smooth, glabrous. Color: When opening and fully opened, upper surface: Close to N87A; towards the base, 155D. When opening and fully opened, lower surface: Close to N87B; longitudinal central stripe, close to 85A. Throat: Close to 151A; venation, close to N79A. Tube: Close to 151D.

*Sepals*.—Quantity: Two per flower. Length: About 5.4 mm. Width: About 1.1 mm. Shape: Lanceolate. Apex: Acute. Base: Obtuse. Margin: Entire. Texture, upper and lower surfaces: Slightly pubescent. Color, upper surface: Close to 137B. Color, lower surface: Close to 137C.

*Reproductive organs*.—Androecium: Stamen quantity per flower: About five. Anther shape: Ellipsoidal. Anther size: About 1.3 mm by 0.2 mm. Anther color: Close to 199C and N199C. Pollen: Scarce. Gynoecium: Pistil quantity per flower: One. Pistil length: About 1 cm. Style color: Close to 155B and 199D. Stigma shape: Oblong. Stigma color: Close to 187A. Ovary color: Close to 144B.

*Seeds and fruits*.—Seed and fruit development have not been observed on plants of the new *Scaevola*.

Garden performance: Plants of the new *Scaevola* have been observed to have good garden performance and to tolerate rain, wind and temperatures ranging from about 0° C. to about 40° C.

Pathogen/pest resistance: Plants of the new *Scaevola* have not been shown to be resistant to pathogens and pests common to *Scaevola*.

It is claimed:

1. A new and distinct *Scaevola* plant named 'Bonsca7200' as illustrated and described.

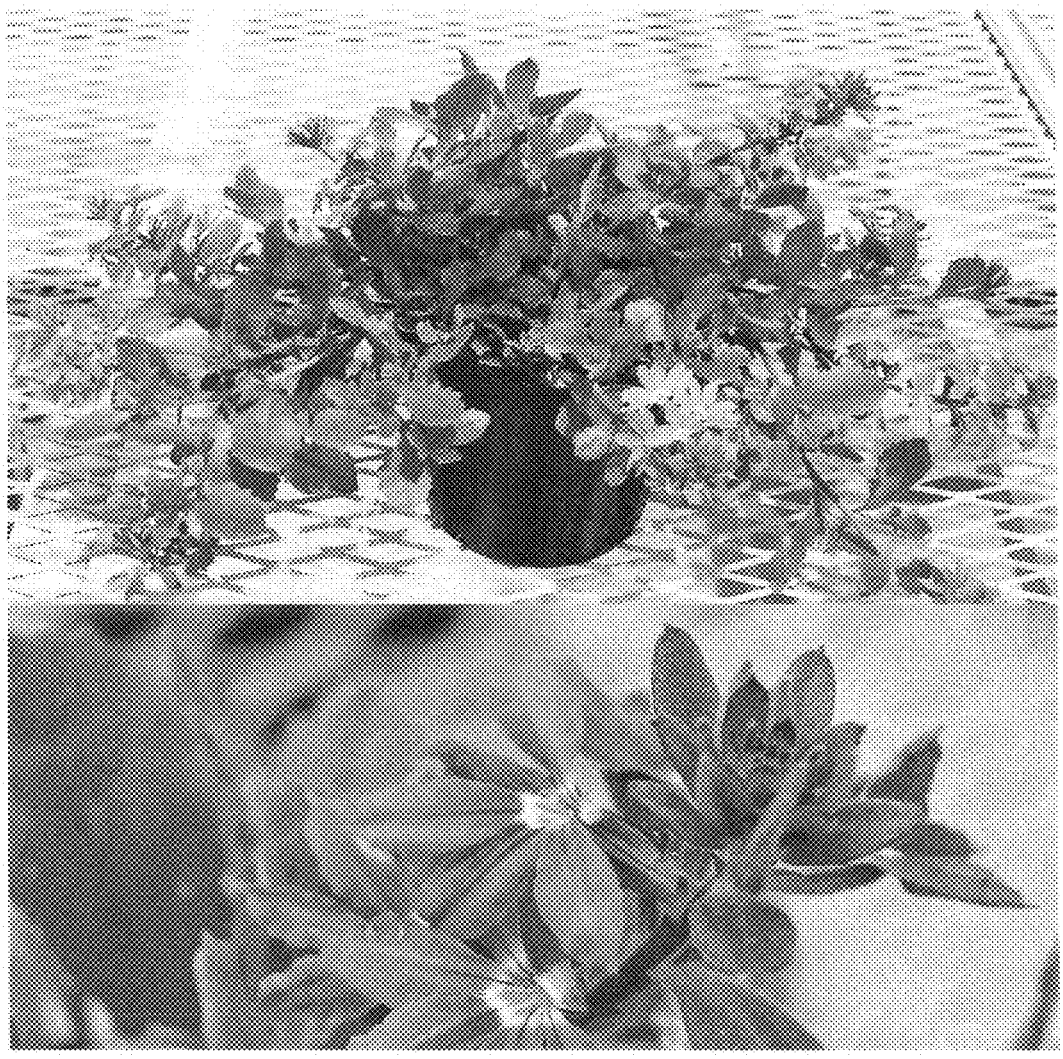

* * * * *